(12) United States Patent
Davidian et al.

(10) Patent No.: US 9,643,164 B2
(45) Date of Patent: May 9, 2017

(54) IRON-BASED CATALYSTS AND TREATMENT PROCESS THEREFOR FOR USE IN FISCHER-TROPSCH REACTIONS

(71) Applicant: Dow Global Technologies LLC, Midland, MI (US)

(72) Inventors: Thomas Davidian, Ghent (BE); Matthijs Ruitenbeek, Terneuzen (NL); Adrianus Koeken, Terneuzen (NL); Marjolein Vos, Terneuzen (NL); Marco F. Wielemaker, Axel (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/894,561

(22) PCT Filed: Jun. 25, 2014

(86) PCT No.: PCT/US2014/043983
§ 371 (c)(1),
(2) Date: Nov. 30, 2015

(87) PCT Pub. No.: WO2014/210089
PCT Pub. Date: Dec. 31, 2014

(65) Prior Publication Data
US 2016/0121311 A1     May 5, 2016

Related U.S. Application Data
(60) Provisional application No. 61/840,648, filed on Jun. 28, 2013.

(51) Int. Cl.
*B01J 37/18*     (2006.01)
*B01J 27/22*     (2006.01)
(Continued)

(52) U.S. Cl.
CPC .............. *B01J 27/22* (2013.01); *B01J 23/78* (2013.01); *B01J 35/002* (2013.01); *B01J 35/006* (2013.01);
(Continued)

(58) Field of Classification Search
CPC ........ B01J 27/22; B01J 35/023; B01J 35/006; B01J 35/002; B01J 37/18; B01J 23/78;
(Continued)

(56) References Cited

U.S. PATENT DOCUMENTS 2,728,786 A * 12/1955 McGrath ............... C07C 1/0445
518/717
4,252,685 A     2/1981 Schlinger et al.
(Continued)

FOREIGN PATENT DOCUMENTS

EP     2314557 A1     4/2011
GB     785116 A       10/1957
(Continued)

OTHER PUBLICATIONS

Bian, et al., "Studies with Precipitated Iron Fisher-Tropsch Catalyst Reduced by H2 or CO," J. of Mol. Catal. A: Chemical, 186, (2002), 203-213.
(Continued)

*Primary Examiner* — Patricia L Hailey
(74) *Attorney, Agent, or Firm* — Dinsmore & Shohl LLP

(57) ABSTRACT

A Fischer-Tropsch catalyst, useful for conversion of synthesis gas to olefins, is prepared from a catalyst precursor composition including iron oxide and an alkali metal on a substantially inert support, and then treated by a process including as ordered steps (1) reduction in a hydrogen-containing atmosphere at a pressure of 0.1 to 1 M Pa and a temperature from 280° C. to 450° C.; (2) carburization in a carbon monoxide-containing atmosphere at a pressure from
(Continued)

Overlay of CO conversion curves as a function of run time (in hours) during FT conditions
for CAT1 treated under different protocols,
including Examples 1-3 and Comparative Examples 1, 2, 3, 5-8.

0.1 to 1 MPa and a temperature from 200° C. to less than 340° C.; and (3) conditioning in a hydrogen- and carbon monoxide-containing atmosphere at a pressure from 0.1 to 2 MPa and a temperature from 280° C. to 340° C. The resulting catalyst exhibits at least one improvement selected from (1) increased overall activity; (2) reduced break-in time; (3) slowed rate of deactivation; and (4) increased time to onset of deactivation; when compared to an otherwise identical catalyst precursor composition treated by one or some, but not all, of the given steps and/or under different conditions.

10 Claims, 4 Drawing Sheets

(51) Int. Cl.
B01J 23/78 (2006.01)
C07C 1/04 (2006.01)
C10G 2/00 (2006.01)
B01J 37/08 (2006.01)
B01J 37/02 (2006.01)
B01J 35/00 (2006.01)
B01J 35/02 (2006.01)

(52) U.S. Cl.
CPC ......... B01J 35/0013 (2013.01); B01J 35/023 (2013.01); B01J 37/0205 (2013.01); B01J 37/084 (2013.01); B01J 37/18 (2013.01); C07C 1/0445 (2013.01); C10G 2/332 (2013.01); C07C 2521/04 (2013.01); C07C 2523/745 (2013.01); Y02P 20/52 (2015.11)

(58) Field of Classification Search
CPC . C07C 1/044; C07C 1/0445; C07C 2523/745; C07C 2523/78; C10G 2/332; Y02P 20/52
USPC .......... 502/177, 184, 185; 518/717, 719–721
See application file for complete search history.

(56) References Cited

U.S. PATENT DOCUMENTS

| 4,256,654 A | | 3/1981 | Schlinger et al. | |
| 4,548,953 A | * | 10/1985 | Fiato | B01J 27/22 518/717 |
| 4,559,365 A | * | 12/1985 | Wachs | B01J 27/22 518/717 |
| 4,584,323 A | | 4/1986 | Soled et al. | |
| 2004/0122115 A1 | | 6/2004 | Espinoza et al. | |
| 2008/0015266 A1 | | 1/2008 | Yakobson et al. | |
| 2009/0111684 A1 | * | 4/2009 | Demirel | B01J 23/745 502/158 |
| 2014/0360917 A1 | * | 12/2014 | Park | C10G 2/332 208/14 |

FOREIGN PATENT DOCUMENTS

| GB | 2473071 A | 3/2011 |
| WO | 2008/009076 A2 | 1/2008 |
| WO | 2009022262 A2 | 2/2009 |

OTHER PUBLICATIONS

Bukur et al., "Activation Studies with a Precipitated Iron Catalyst for Fischer-Tropsch Synthesis", J. Catal., (1995), 366-375, 155.
Bukur et al., "Activation Studies with a Promoted Precipitated Iron Fischer-Tropsch Catalyst", Ind. Eng. Chem. Res. (1989), 1130-1140, 28.
Datye et al., "The Role of Catalyst Activation on the Activity and Asstrition of Precipitated Iron Fischer-Tropsch catalysts", Stud. Surf. Sci. Eng., (1997), 169-174, 107.
H.M. Torres Galvis, et al., "Supported Nanoparticles as Catalysts for Sustainable Production of Lower Olefins", Science (2012), 835-838, 335.
Luo et al., "Fischer-Tropsch synthesis catalyst activation of low alpha iron catalyst" Catalysis Today, (2009), 127-134, 140.
Shroff, et al., "Activation of Precipitated Iron Fischer-Tropsch Synthesis Catalysts," J. Catal., (1995), 185-207, 156.
PCT/US2014/043983, 2nd Written Opinion of the International Searching Authority mailed Jul. 13, 2015.
PCT/US2014/043983, International Preliminary Report on Patentability mailed Oct. 19, 2015.
PCT/US2014/043983, International Search Report and Written Opinion of the International Searching Authority mailed Oct. 7, 2014.
PCT/US2014/043983, Response Written Opinion dated Apr. 28, 2015.

* cited by examiner

Overlay of CO conversion curves as a function of run time (in hours) during FT conditions for CAT1 treated under different protocols, including Examples 1-3 and Comparative Examples 1, 2, 3, 5-8.

Legend:

Example 10 (◇)

Example 11 (△)

Example 12 (◁)

Comparative Example 13 (▽)

Comparative Example 14 (○)

Comparative Example 15 (□)

Overlay of CO conversion curves as a function of run time (in hours) during FT conditions for CAT2 treated under different activation conditions, including Examples 10-12 and Comparative Examples 13-15.

Legend:

Example 13 (△)

Example 14 (□)

Example 15 (◇)

Comparative Example 16 (○)

Comparative Example 17 (▽)

Comparative Example 18 (◁)

Overlay of CO conversion curves as a function of run time (in hours) during FT conditions for CAT3 treated under different activation conditions, including Examples 13-15 and Comparative Examples 16-18.

Particle size distribution by measuring analyzing TEM micrographs of
catalyst samples obtained after Example 1 and Comparative Example 8.
Graph on left shows Comparative Example 8 and graph on right shows Example 1.

IRON-BASED CATALYSTS AND TREATMENT PROCESS THEREFOR FOR USE IN FISCHER-TROPSCH REACTIONS

CROSS-REFERENCE TO A RELATED APPLICATION

The present application claims priority to U.S. Patent Application Ser. No. 61/840,648, filed Jun. 28, 2013, which is incorporated herein by reference in its entirety.

The invention relates to the field of iron-based catalysts useful for the conversion of synthesis gas to light olefins. More particularly, the invention relates to a process for improving the performance of such catalysts with respect to maximum activity, break-in period, deactivation rate and/or time to onset of deactivation.

The invention generally applies to the conversion of synthesis gas. Synthesis gas (or "syngas") refers herein to a mixture comprising carbon monoxide and hydrogen. Synthesis gas may also comprise carbon dioxide. For use in the production of olefins by means of a Fischer-Tropsch (FT) process, the $CO_2$ is preferably removed, reduced, or otherwise adjusted so as to provide the desired $H_2$:CO ratios discussed below.

Synthesis gas is generally produced by methods such as steam reforming, partial oxidation, dry reforming or autothermal reforming of natural gas or heavier hydrocarbons to produce hydrogen and carbon monoxide, or the gasification of coal, of biomass, and in some types of waste-to-energy gasification facilities. Particularly with reference to its potential biomass and waste origin, synthesis gas is increasingly receiving attention as an environmentally friendly, sustainable source of carbon-based chemicals.

Useful applications of synthesis gas will generally require chemical conversion of the gaseous CO and $H_2$ components into hydrocarbons such as fuels or chemicals by, e.g., Fischer-Tropsch synthesis, which commonly employs catalysts based on iron or cobalt. Nickel- and ruthenium-based catalysts may alternatively be used. The principal purpose of this process is to produce a synthetic petroleum substitute, typically from coal, natural gas or biomass, for use as synthetic lubrication oil or as synthetic fuel.

The Fischer-Tropsch process involves a variety of competing chemical reactions, which lead to a series of desirable products and, often, undesirable byproducts. When using cobalt catalysts, the most important reactions are those resulting in the formation of alkanes. These can be described by the chemical equation:

$$(2n+1)H_2 + nCO \rightarrow C_nH_{(2n+2)} + nH_2O \quad \text{Formula 1}$$

with n being a positive integer. Since methane (n=1) is mostly considered an unwanted byproduct, process conditions and catalyst composition are usually chosen to favor higher molecular weight products (n>>1) and thus minimize methane formation. In addition to alkane formation, competing reactions result in the formation of alkenes, as well as alcohols and other oxygenated hydrocarbons. Usually, only relatively small quantities of these non-alkane products are formed, although iron-based catalysts favoring some of these products have been developed. The formation of alkenes generally is represented as some combination of the following chemical equations, with Formula 1 representing the extreme of water formation, and Formula 2 representing the extreme of carbon dioxide formation, i.e., the water-gas shift reaction:

$$2nH_2 + nCO \rightarrow C_nH_{2n} + nH_2O \quad \text{Formula 2}$$

$$CO + H_2O \rightarrow H_2 + CO_2 \quad \text{Formula 3}$$

The combination of the above two reactions is represented by Formula 4.

$$nH_2 + 2nCO \rightarrow C_nH_{2n} + nCO_2 \quad \text{Formula 4}$$

It is generally recognized that cobalt catalysts tend to follow Formula 2 hereinabove, while iron catalysts drive the reaction toward Formula 3 as a result of the water-gas shift reaction.

The FT process may be operated in the temperature range of 200 degrees Celsius (° C.) to 300° C., i.e., as a "Low Temperature Fischer-Tropsch" (LTFT) reaction, or in the temperature range of 300° C. to 350° C., especially 330° C. to 350° C., i.e., as a "High Temperature Fischer-Tropsch" (HTFT) reaction. Higher temperatures may lead to faster reactions and higher conversion rates, but may also tend to favor undesired methane production and faster or earlier-onset deactivation. Cobalt-based catalysts may be preferentially employed for LTFT reactions, while iron-based catalysts may be preferred for higher temperature LTFT and HTFT reactions. Increasing the pressure in either type of reaction may enhance catalytic activity as well as increase formation of long-chain alkanes, which may be desirable for fuel production, but is often undesirable for the production of chemicals. Applying iron-based catalysts at higher temperature, 300° C. and higher, usually results in a shift to lower molecular weight products, such as ethylene and propylene, i.e., the lower olefins, while lower temperatures, e.g., 240° C. to 280° C., may result in longer alkane chains. Thus, those skilled in the art will generally balance temperatures, pressures, and catalyst selections to increase yields of desired compounds and reduce yields of undesired or less desired compounds. See also, e.g., H. M. Torres, et al., "Supported Nanoparticles as Catalysts for Sustainable Production of Lower Olefins", Science 2012 335, 835-838.

Regardless of selections of ultimate operating conditions, typical FT conversion processes will generally include a "break-in" period, which is the time during which the catalyst's activity (and productivity) increases until a maximum activity level is reached. After a certain period of time, the catalyst will begin to deactivate, until it reaches a point at which it is necessary or desirable to either regenerate or replace the catalyst. It should be noted that the break-in period may last 100 hours (h) or more, and therefore break-in time represents less-than-maximum production and correspondingly undesirable economic impact. Accordingly, it is generally considered desirable to minimize the break-in period, to ensure that the catalyst maximum activity is as high as possible from the start. Furthermore, it is desirable to delay the onset of deactivation and/or reduce the rate of deactivation. Researchers have therefore sought means and methods to accomplish any or all of these goals.

It is generally accepted in the art that, in the case of a supported catalyst, decreasing the size of the catalytic particles may enhance activity. This is because smaller particles have a greater metallic surface area to contact the reactant mixture. Thus, many researchers have attempted to produce catalysts having very small and well-dispersed particles, but frequently their approaches involve complex synthesis methods and/or use of expensive additives, thus increasing the overall cost of producing the catalysts. Another problem is that small particles may aggregative or sinter during the reaction, thereby nullifying their benefit or creating an additional problem to be solved. Regardless of particle size, however, researchers generally recognize the desirability or even necessity of some type of activation process that is needs to be performed in order to ensure appropriate catalytic activity.

For example, EP 2 314 557 A1 discloses a Fischer-Tropsch to olefins (FTO) process featuring a supported, iron-based catalyst wherein the support is inert toward the iron and the iron is in the form of particles of an organic iron complex that decomposes under heat to form iron oxide nanoparticles. A multi-step activation is carried out that includes a reduction in $H_2$/Ar at 350° C. for 2 h; feeding of a $H_2$/CO (i.e., synthesis gas) mixture at 280° C. and 20 bar (2 megapascal, MPa) pressure; introduction of syngas and heating up to 340° C., at which temperature it is maintained for 6 h; a cooldown to 280° C. for 33 h; and finally, resumption of temperature at 340° C.

WO 2009 02222 A2 discloses a method of activating an iron-based Fischer-Tropsch catalyst by contacting with a reducing gas, such as syngas, at a temperature from 245° C. to less than 280° C. and pressure from greater than 0.5 MPa to 2.2 MPa, at a gas hourly space velocity (GHSV) of at least 6000 milliliter-Newtons per gram catalyst per hour (mL (N)/g cat/h) to reduce the iron.

WO 2008 009076 A1 discloses activation of an unsupported iron-based catalyst in a slurry vessel under $H_2$, CO and an inert gas, with a ratio of inert to $H_2$ and CO from 3 to 4. Temperature is from 270° C. to 280° C., and pressure ranges from 140 psia (0.97 MPa) to 160 psia (1.10 MPa).

A literature article by Luo, et al., "Fischer-Tropsch synthesis catalyst activation of low alpha iron catalyst," *Catalysis Today*, 140, 127 (2009), reported work with a precipitated, low alpha iron-based catalyst. That work investigated three different activation treatments, using, separately, $H_2$, CO, and syngas, under various conditions. Those studies showed that both activation gas selection and operational conditions during the Fischer-Tropsch to olefins process had an effect on the ultimate productivity.

Shroff, et al., "Activation of Precipitated Iron Fischer-Tropsch Synthesis Catalysts," *J. Catal.*, 156 (1995), 185-207 investigated the activation of precipitated iron-based catalysts for the LTFT reaction. They found that the break-in time was shorter and the activity was higher for a catalyst activated under CO at 543K compared to the same catalyst activated under $H_2$ at the same temperature. However, the activity of the catalyst activated under CO quickly dropped and after 40 hours both samples had the same conversion rate. Both catalysts were more active than a catalyst exposed directly to syngas under reaction conditions including a temperature of 523K.

Bian, et al., "Studies with Precipitated Iron Fisher-Tropsch Catalyst Reduced by $H_2$ or CO," *J. of Mol. Catal. A: Chemical*, 186, (2002), 203-213, investigated the activation of precipitated iron bulk catalysts for an LTFT reaction at 250° C. and a ratio of $H_2$:CO of 2:1. They found that CO treated samples had the highest FT activity. Samples reduced under $H_2$, then treated under CO had somewhat higher activity than the $H_2$-only reduced samples but had longer break-in time and faster deactivation rate. Despite these various approaches, there remains a need in the art to further increase overall productivity levels, by reducing break-in times, increasing activity, slowing deactivation rates and/or delaying deactivation onset of catalysts that are used in FTO processes.

In one aspect the invention provides a process for producing an iron-based catalyst comprising sequential steps in order as follows: (1) subjecting a catalyst precursor composition that comprises iron oxide and at least one alkali metal on a particulate support, the iron oxide being present in an amount ranging from 1 percent by weight (wt %) to 20 wt % based upon combined weight of iron and particulate support, the at least one alkali metal being present in an amount from greater than 0 mole percent (mol %) to 10 mol %, based upon moles of iron present in the catalyst precursor, to reduction in a hydrogen-containing atmosphere at a hydrogen partial pressure ranging from 0.1 megapascal (MPa) to 1 MPa at a temperature from 300° C. to 475° C. to produce an at least partially reduced catalyst precursor composition; (2) subjecting the at least partially reduced catalyst precursor composition to carburization in a carbon monoxide-containing atmosphere at a carbon monoxide pressure ranging from 0.1 MPa to 1 MPa and a temperature ranging from 200° C. to less than 340° C., to produce an at least partially carburized catalyst precursor composition; and (3) subjecting the at least partially carburized catalyst precursor composition to conditioning in an atmosphere containing at least hydrogen and carbon monoxide in a molar ratio ranging from 0.5 to 3, wherein the combined hydrogen and carbon monoxide gas pressures total from 0.1 MPa to 2 MPa, at a temperature from 200° C. to 340° C., to produce an at least partially conditioned, particulate catalyst that comprises iron carbide.

Figure 1:
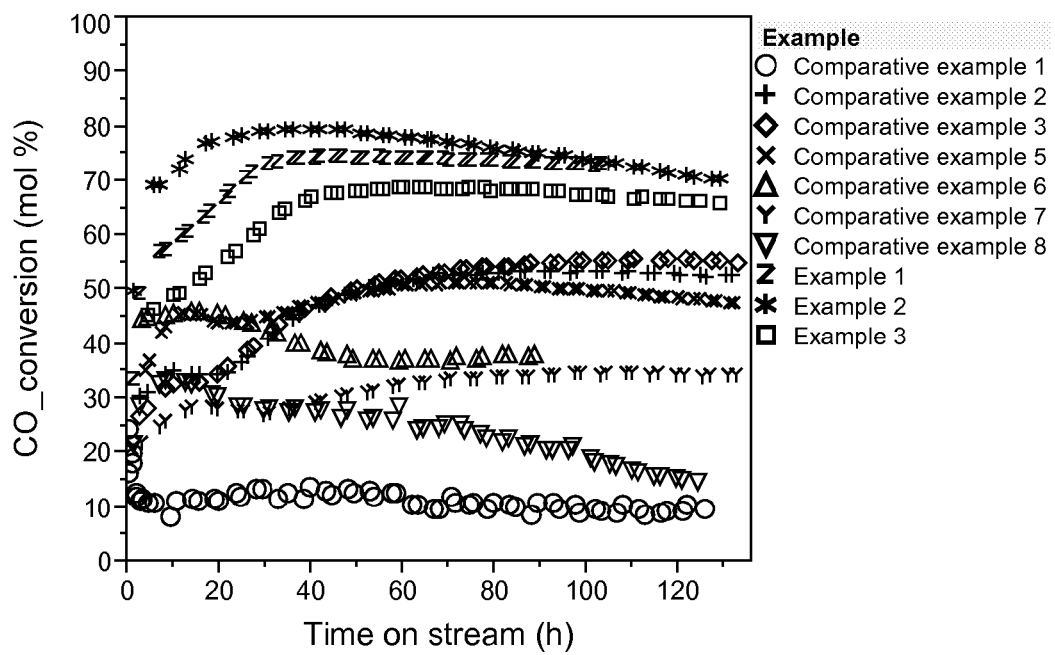
FIG. 1 is a graphic overlay of CO conversion curves as a function of run time (in hours) for a catalyst (CAT1) treated under different protocols, including Examples 1-3 and Comparative Examples 1, 2, 3, 5-8

The invention generally provides a process to prepare a supported, iron-based catalyst that may be characterized as having at least one of the following characteristics leading to improved productivity: (1) a reduced break-in time when employed in a Fischer-Tropsch reaction to convert synthesis gas to light olefins; (2) a higher overall activity; (3) a slower deactivation rate; and/or (4) an increased time to onset of deactivation; when compared to another otherwise identical iron-based catalyst that has not been treated according to the process of the invention. Because of these advantageous features, reactor size may be reduced because of overall higher throughputs, and therefore costs may be concomitantly decreased. Without wishing to be bound by any single theory, it is suggested that the improvements seen in the present invention may be attributable to the effect and/or a synergism between the formation of catalyst particles exhibiting greater uniformity and very small size, improved dispersion of such particles on the support, a larger number of active iron carbide domains, and/or more stable iron carbide domains.

The process of the invention includes in a first step formation of an appropriate catalyst precursor composition. Such catalyst precursor composition includes at least two catalytic components: (1) an iron oxide; and (2) an alkali metal. A third and necessary component is a suitable support. Each will be addressed below in greater detail.

The iron oxide may be initially obtained from a variety of iron-containing compounds, through different preparation methods. Examples of iron-containing compounds are inorganic and organic iron salts, iron chelates, iron clusters, iron hydroxides and oxy-hydroxides, and iron organometallic complexes. Non-limiting representatives of these compounds may include, for example, iron tetracarbonyl, iron pentacarbonyl, iron nonacarbonyl, iron nitrates, bromides, chlorides, fluorides, phosphates, sulfates, acetylacetonates, acetates, fumarates, gluconates, citrates, benzoates, maleates, oxalates, oleates, stearates, and the like. Thus, the iron-containing compound may provide iron to the catalyst precursor composition in a ferrous form, a ferric form, or a combination thereof. In particular embodiments the starting iron-containing compound preferably comprises Fe(II) or Fe(III) in combination with organic ligands or anions such as acetate, citrate, EDTA (ethylene diamine tetra acetate) or NTA (nitrilo triacetate) and, in certain embodiments, may include iron(II) carboxylate compounds, e.g., hydroxy-carboxylic iron compounds including ammonium, sodium or potassium salts, and ammonium iron citrate. One particularly convenient form of iron-containing starting compound may be ammonium iron(III) citrate.

The catalyst precursor composition also includes at least one alkali metal. Suitable alkali metals may be conveniently selected from lithium (Li), sodium (Na), potassium (K), rubidium (Rb), cesium (Cs) and combinations thereof, and in particular embodiments, K, Na, and combinations thereof. Starting materials may include, in non-limiting example, salts of the selected alkali metal such as alkali nitrates, alkali acetates, alkali carbonates, alkali sulfates, and combinations thereof. In certain embodiments alkali sulfates may be preferred.

The catalyst precursor composition of the invention is dispersed onto a support. Without wishing to be bound by theory, it is suggested that the supported nature of the catalyst prepared by the inventive process plays an important role in its efficacy, particularly in comparison with bulk (unsupported) catalysts. In the present invention it is therefore desirable that the selected support be particulate. In certain particular embodiments preferred supports may be selected from oxidic materials such as alpha-alumina, zirconia and titania; carbon-based materials such as silicon carbide and carbon nanofibers; and combinations thereof. Carbon-based materials preferably have a surface area less than 500 m$^2$/g, and more preferably less than 200 m$^2$/g, while oxidic supports preferably have a surface area less than 100 m$^2$/g, more preferably less than 50 m$^2$/g, and most preferably less than 15 m$^2$/g.

Once the iron-containing compound and the alkali metal-containing compound are selected, such are incorporated onto the support using means and methods that are well known to those skilled in the art. Such may include, for example, incipient wetness impregnation of an aqueous solution containing an iron salt and an alkali metal salt, with each impregnation followed by drying at, e.g., 120° C. This ensures deposition of the iron and alkali metal promoter(s) on the support. Other suitable means of depositing the iron oxide particles onto the support may include wet impregnation, chemical vapor deposition, homogenous deposition precipitation, and any other technique known to those skilled in the art. Regardless of method, however, it is important to note that such should include a thermal treatment, e.g., a calcination, which operates to substantially decompose the iron-containing compound to form iron oxide species. For this purpose heating at a temperature ranging from 400° C. to 600° C., frequently for a time ranging from 1 hour (h) to 24 h, is usually sufficient to accomplish substantial decomposition of the iron oxide species.

It is generally preferred that the proportion of iron-containing compound used to prepare the catalyst precursor composition represent from 1 weight percent (wt %) to 20 wt %, more preferably from 1 wt % to 10 wt %, based on the combined weight of the iron-containing compound and the support. It is also preferred that the proportion of the alkali metal compound represent from greater than 0 mol % to 10 mol %, more preferably from 1 mol % to 5 mol, based on moles of iron in the iron-containing compound. While clustering of iron oxide particles may occur, it is desired that at least 1 wt %, preferably at least 10 wt %, be in direct contact with the support, where chemical interactions will help to ensure maintenance of the catalytic substrate.

In certain embodiments of the invention at least one alkaline earth metal may be included in the catalyst precursor composition. Such may be selected from, for example, magnesium (Mg), calcium (Ca), strontium (Sr), barium (Ba) and combinations thereof, with Mg, Ca and Ba being preferred in some embodiments, and preparation may therefore begin with salts thereof, such as alkaline earth nitrates, alkaline earth acetates, alkaline earth carbonates, and combinations thereof. It is strongly preferred that cobalt not be included in the composition. Such may be particularly undesirable where the catalyst will be employed in an HTFT process because it may decrease the selectivity to olefins and increase paraffin, particularly methane, production. In proportion it is preferred that the alkaline earth metal is present in the catalyst precursor composition in an amount ranging from 0 mol % to 10 mol %, more preferably from 1 mol % to 5 mol %, based on the combined weight of the iron-containing compound and the support. Similar techniques would be employed for inclusion of an alkaline earth metal as described hereinabove for an alkali metal.

As indicated above, a supported catalyst will be understood as pertaining to a catalyst composition comprising a catalytically active part (i.e., particles as provided that are either active, or are converted into an active phase in situ), and a catalytically non-active part, wherein the catalytically non-active part (the support) generally forms the majority of the catalyst. This distinguishes a supported catalyst from a bulk catalyst, in which the catalytically non-active part is generally the minority. Thus, in the supported catalyst of the invention, the catalytically non-active part is generally more than 50 wt % of the catalyst composition. Preferably the support forms more than 60 wt %, and more preferably more than 80 wt % of the total catalyst composition.

Once the precursor composition is prepared as previously described it is ready to be subjected to the process steps of the invention. This process is defined herein as essentially a three-step process, and it is noted that omission of any of the three steps, and/or alteration in the order of the steps, is expected to result in a catalyst displaying, in at least one of the hereinafter-defined ways, a less desirable performance characteristic than would be displayed if the invention is carried out. As previously noted, the goal with respect to the performance characteristic is (1) a relative reduction in break-in time, and/or (2) a relative increase in highest productivity level attained, and/or (3) a relative reduction in rate of deactivation, and/or (4) a relative increase in time prior to onset of deactivation. As the term is used herein, "relative" means in comparison with an identical catalyst precursor composition that has not been subjected to the three steps of the inventive process in the defined order.

The first step of the inventive process is a reduction step that involves exposure of the catalyst precursor composition to a hydrogen ($H_2$)-containing atmosphere at a temperature ranging from 280° C. to 450° C., more desirably from 340° C. to 425° C. The $H_2$ is preferably a flowing atmosphere at a hydrogen pressure from 0.1 MPa to 1 MPa, more desirably from 0.3 MPa to 1 MPa. While pure $H_2$ is preferred, the atmosphere may contain a proportion of other gases and particularly inert gases such as nitrogen, noble gases, and/or carbon dioxide, in which case the 0.1 MPa to 1 MPa limits refer to hydrogen partial pressure. However, it will be obvious to those skilled in the art that any gas that would significantly oxidize the catalyst precursor composition should desirably not be present in any amount greater than 3 volume percent (vol %), and preferably not greater than 0.01 vol %. The temperature and exposure are maintained for a time sufficient to at least partially reduce the catalyst precursor composition. As the term is used herein, "reduced" means that the iron oxide species present as a result of the preparation of the catalyst precursor composition has been converted to a lower oxidation state. Therefore, the at least partially reduced catalyst will comprise a higher fraction of magnetite ($Fe_3O_4$), FeO, metallic iron Fe, or a mixture thereof, than the iron oxide, which generally comprises a predominant fraction of hematite ($Fe_2O_3$). A suitable duration for this first inventive step in the conditions described above is, in certain embodiments, from 1 h to 6 h.

The extent of reduction desired will be empirically determined by the skilled practitioner according to desired results, costs, and the like. However, it is generally desired that reduction be carried out such that at least about 80 wt % of the iron oxide has been converted to a lower oxidation state, and more preferably at least about 90 wt %. Characterization tools that may be employed to determine the extent of reduction, i.e., to characterize the at least partially reduced catalyst precursor composition, may include, for example, X-ray absorption spectroscopy, X-ray diffraction, Mossbauer spectroscopy, and the like.

Following the first step, the now at least partially reduced catalyst precursor composition is then subjected to a carburization step, wherein it is exposed to a CO-containing atmosphere, having a CO partial pressure ranging from 0.1 MPa to 1 MPa, preferably from 0.3 MPa to 1 MPa. The atmosphere may also include a proportion of other gases, including inert gases such as nitrogen or noble gases, carbon dioxide, or a combination thereof, but it is preferred that at least 50 volume percent (vol %), more preferably at least 90 vol %, be CO. The carburization gas mixture should contain less than 50 vol % hydrogen or other reducing gas, preferably less than 10 vol % more preferably less than 1 vol %. In this step, the temperature desirably ranges from 200° C. to less than 340° C., more desirably from 280° C. to 340° C.

The result of step 2 is an at least partially carburized catalyst. As the term is used herein, "carburized" means that the iron oxide species formed during the reduction step are converted to an iron carbide species. Iron carbide species may include, but are not limited to, cementite ($Fe_3C$), Hägg carbide ($Fe_5C_2$), Eckstrom and Adcock carbide ($Fe_7C_3$), hexagonal carbide ($Fe_2C$ and $Fe_{2.2}C$), and mixtures thereof. Without wishing to be bound by any theory, it is suggested that the alkali metal and, if included, alkaline earth metal operate as catalyst promoters, which means that during the carburization they increase the rate of formation of the iron carbide species and reduce methane formation by favoring the production of longer chain hydrocarbons. A suitable duration for the carburization step in the conditions described hereinabove may be, for example, a time period from 1 h to 6 h.

As in the case of reduction, those skilled in the art may determine empirically the acceptable or desired level of carburization to be achieved. However, it may be assumed that full carburization of all iron oxides within the particle is not required, and that the particular concern is optimization of carburization at or near the surface of the catalyst particle to ensure concomitant optimization of catalytic activity. Characterization tools that may be employed to determine the fact and/or extent of carburization, i.e., to characterize the at least partially carburized catalyst precursor composition, may include those of the same types used to determine the extent of reduction in step 1, for example, X-ray absorption spectroscopy, X-ray diffraction, Mossbauer spectroscopy, and the like.

Finally, in a third step, the at least partially carburized catalyst precursor composition is "conditioned." As the term is used herein, "conditioned" means that the carburized catalyst precursor composition is brought into contact with the synthesis gas feedstock in which it will be employed in an FTO process, under specific conditions that result in formation of the final catalyst. It is hypothesized that conditioning reduces the likelihood of subsequent ensure sintering or coking of the catalyst during the FTO process and increases maintenance of the carbide phases that were formed during the carburization step. This final catalyst is also further defined as exhibiting its full catalytic abilities thereafter in the FTO process.

The conditioning step includes contacting the at least partially carburized catalyst precursor composition to an atmosphere comprising $H_2$ and CO, which may be most conveniently the synthesis gas feedstock to be used in the FTO process thereafter but which may be any mixture of $H_2$ and CO, provided that the atmosphere contains an $H_2$:CO mole ratio ranging from 0.5 to 3, and that there is a maximum of 50 vol % of inert gas such as nitrogen or a noble gas, and preferably no more than 10 vol %. The $H_2$/CO mixture may be introduced at a temperature ranging from 200° C. to 340° C., preferably from 280° C. to 340° C., and at a relatively low pressure, i.e., desirably from 0.1 MPa to 2 MPa, more preferably from 0.1 MPa to 1 MPa, The result of step 3 is the final catalyst.

Determination of the extent or degree of the conditioning step is, as with the previously described steps, primarily empirical in nature, with routine experimentation enabling the skilled routineer to determine the point at which the transition from "conditioning" to "running the FTO reaction" most effectively takes place. This transition includes at least one of a change in temperature, a change in pressure, a change in synthesis gas composition, or a combination thereof, such change bringing the identified parameter out of the range described in the preceding paragraph. Determination of the efficacy of the conditioning step may most conveniently be made by a reduction in break-in time in comparison with an otherwise identical catalyst that has not undergone the three-step treatment as defined hereinabove, but evidence to support any of the other improvements that may be obtained by practice of the invention, including increase in maximum activity, reduction in rate of deactivation, and/or increase in time until onset of deactivation will also establish the efficacy of the invention.

An important feature of the invention is that, once the appropriate catalyst precursor composition has been subjected to each of the steps of the invention, the desirable result will be a supported catalyst wherein the catalyst particles are generally smaller and of narrower size distribution than those exhibited by identical precursor compositions that are "activated" or otherwise converted to final catalysts under a different process. In the final catalyst of the present invention, the iron-containing particles that are dispersed on the support preferably have a particle size of less than 50 nanometers (nm), more preferably less than 30 nm, still more preferably less than 20 nm; a mean particle size ranging from 5 nm to 7 nm; and a particle size distribution wherein at least 90 wt % of the particles range from 2 nm to 9 nm.

The result of the invention is an iron-based catalyst that exhibits a higher activity and/or reduced break-in period and/or slower deactivation and/or increased time before onset of deactivation than an otherwise identical catalyst that has not been subjected to the three steps of the invention as described hereinabove and in the order described hereinabove. In particular embodiments, the catalyst may exhibit a break-in period that is shorter by at least 10%, preferably at least 20%, in comparison with that of a catalyst prepared from an identical catalyst precursor composition, but without at least one of step (1) and step (2). The catalyst may also exhibit a maximum carbon monoxide conversion percentage that is greater by at least 5%, preferably at least 10%, in comparison with the maximum CO conversion percentage exhibited by a catalyst prepared from an identical catalyst precursor composition, but without at least one of step (1) and step (2). Finally, and also in particular embodiments, the catalyst may preferably exhibit a deactivation rate that is reduced by at least 50%, more preferably at least 75%, in comparison with the deactivation rate of a catalyst prepared from an identical catalyst precursor composition, but without at least one of step (1) and step (2).

Such a catalyst may be suitable for use in a variety of processes, including but not limited to Fischer-Tropsch reactions to prepare olefins, such as ethylene and propylene from synthesis gas, and preferably specifically LTFT reactions.

EXAMPLES AND COMPARATIVE EXAMPLES

Catalyst Preparation

CAT1: 5 wt % Fe, 2% mol K/mol Fe, NORPRO™ SA5162 (1+/−0.2 m$^2$/g)

A first catalyst precursor composition, containing 5 wt % Fe and 2 mol % K/mol Fe supported on alpha-alumina, is prepared. 5.26 grams (g) of ammonium iron citrate (FLUKA™ 16.2 wt % Fe, available from Sigma-Aldrich) and 0.029 g of potassium nitrate (Sigma-Aldrich) compounds are dissolved in 12 g de-ionized water and impregnated onto 15 g of an alpha-alumina support (NORPRO™ SA5162; NORPRO™ is a tradename of Saint-Gobain Nor-Pro Corporation) by the incipient wetness impregnation technique. The alpha-alumina support material is received in the form of cylindrical, 3 millimeter (mm) diameter by 3 mm length, extrudate particles, which are then crushed and sieved, the fraction of particles having a U.S. mesh size from 20 to 40 (400 to 841 micrometer, km, diameter) being thereafter used for impregnation. Two impregnation steps are required to impregnate the desired amount of compounds and each step is followed by drying for 1 h at 120° C. in an oven. The resulting material is then calcined in static air at 500° C. for 4 h to yield the catalyst precursor composition that is herein denominated CAT1.

CAT2: 5 wt % Fe, 2% mol K/mol Fe, BASF™ AL-4196 (10+/−2 m$^2$/g)

A second catalyst precursor, containing 5 wt % Fe and 2 mol % K/mol Fe supported on alpha-alumina is prepared. 3.48 g of ammonium iron citrate (FLUKA™, 15.1 wt % Fe) and 0.0188 g of potassium nitrate (Sigma-Aldrich) compounds are dissolved in 6.67 g de-ionized water and impregnated onto 10 g of an alpha-alumina support (BASF™ AL-4196 E1/12, U.S. mesh size 20 to 40 (400 to 841 μm diameter)) by the incipient wetness impregnation technique. (BASF™ is a tradename of BASF—The Chemical Company.) The alpha-alumina support material is received in the form of cylindrical, 1 mm diameter by 12 mm length, extrudate particles, which are then crushed and sieved, the fraction of particles having a U.S. mesh size from 20 to 40 (400 to 841 μm diameter) being thereafter used for impregnation. Four impregnation steps are required to impregnate the desired amount of compounds and each step is followed by drying for 1 h at 120° C. in an oven. The resulting material is then calcined in static air at 500° C. for 4 h to yield the catalyst precursor composition denominated CAT2.

CAT3: 17 wt % Fe, 2% mol K/mol Fe, NORPRO™ SA5162 (1+/−0.2 m$^2$/g)

A third catalyst precursor composition, containing 17 wt % Fe and 2 mol % K/mol Fe supported on alpha-alumina is prepared. Compound solution #1 is prepared by dissolving 3.51 g of ammonium iron citrate (FLUKA™, 15.1 wt % Fe) and 0.0190 g of potassium nitrate (Sigma-Aldrich) in 6.68 g de-ionized water. Compound solution #1 is then impregnated onto 7.5 g of an alpha-alumina support (NORPRO™ SA5162, U.S. mesh size 20 to 40 (400 to 841 km diameter) by the incipient wetness impregnation technique. The alpha-alumina support material is received in the form of cylindrical, 3 mm diameter by 3 mm length, extrudate particles, which are then crushed and sieved, the fraction of particles having a U.S. mesh size from 20 to 40 (400 to 841 μm diameter) being thereafter used for impregnation. After 10 repeated impregnation steps the material is then calcined in static air at 500° C. for 4 h. After the first calcination the remainder of compound solution #1 is impregnated on the catalyst precursor material in one impregnation step.

Precursor solution #2 is prepared by dissolving 3.51 g of ammonium iron citrate (FLUKA™, 15.1 wt % Fe) and 0.0191 g of potassium nitrate (Sigma-Aldrich) in 6.92 g de-ionized water. Seven impregnation steps are required to impregnate precursor solution #2 on the catalytic material and each step is followed by drying for 1 h at 120° C. in an oven. The resulting material is then calcined for the second time in static air at 500° C. for 4 h.

Precursor solution #3 is prepared by dissolving 3.51 g of ammonium iron citrate (FLUKA™, 15.1 wt % Fe) and 0.0193 g of potassium nitrate (Sigma-Aldrich) in 6.07 g de-ionized water. Seven impregnation steps are required to impregnate precursor solution #3 on the catalytic material and each step is followed by drying for 1 h at 120° C. in an oven. The resulting material is then calcined for the third and last time in static air at 500° C. for 4 h to yield the catalyst denominated CAT3. The resulting catalyst contains 21 g of Fe per 100 g support, amounting to an iron content of 17 wt %.

Catalyst Testing

Catalytic activity tests are performed in a fixed bed tubular reactor. An amount, 0.414 g of CAT1, or 0.414 g of CAT2, or 0.35 g of CAT3, accordingly, is mixed with 2.5 mL (equivalent to 2.5 cubic centimeters (cm$^3$)) of silicon carbide and placed at the center of the reactor packed between layers of silicon carbide material. Treatment conditions are varied as described subsequently hereto and the resulting effect on the break-in period and maximum conversion level is monitored. Time on stream "0" is defined as the moment when the FTO reaction conditions are achieved, including a temperature of 340° C., 2 MPa pressure, and the desired synthesis gas H$_2$:CO molar feed ratio. However, the first 10 hours are considered to be irrelevant because during this period the system is not fully stabilized at the reaction conditions. Break-in period is then defined as the amount of time required for the catalyst to reach its maximum conversion level. This point is generally followed by a period of slow deactivation of the catalyst. The conversion (or CO conversion) is defined here as the ratio between the number of moles of CO that react and the number of moles of CO that are introduced into the reactor, with the ratio expressed in percent (%). It is noted that no adjustment is made to account for whether the "reacted" moles form desired product or a byproduct.

Each Example and Comparative Example includes a summary of whether each of the three defined steps of the inventive process is included therein, and the conditions thereof, following the description, for more convenient reference.

Examples 1-9 and Comparative Examples 1-12
[CAT1]

Example 1

The catalytic test is performed as follows. A fixed amount of CAT1 (0.414 g) is loaded in a tubular reactor and diluted with silicon carbide. The reactor is heated to 425° C. and pressurized to 0.3 MPa under a flow of 50 mL/min nitrogen ($N_2$). After stabilization a $H_2$ stream is flowed at 50 mL/min for 3 h for the reduction step. Then the $H_2$ flow is stopped and replaced by a flow of $N_2$. The reactor temperature is cooled down to 280° C. for stabilization purposes. A 50 mL/min flow of CO is introduced for carburization and this carburization step is continued for 3 h. Then, the reactor temperature is raised at a rate of 8° C./min to the predetermined FTO reaction temperature of 340° C. and the pressure is raised to 2 MPa at a rate of 0.015 MPa/min. The following conditioning/reaction mixture (i.e., the synthesis gas) is then introduced at a rate of 1 mL/min: CO flow of 25 mL/min, $H_2$ flow of 25 mL/min and He flow of 5 mL/min, i.e., the $H_2$:CO ratio is 1. The reaction is maintained for 10 days. The break-in period is noted to be 46 h and the CO conversion reaches a maximum of 74%.
(1) Reduction in $H_2$ at 425° C., 0.3 MPa
(2) Carburization in CO at 280° C., 0.3 MPa
(3) Conditioning at 280° C., 0.3 MPa Example 2

The CAT1 (0.414 g) is loaded and diluted as in Example 1. The reactor is heated to 340° C. and pressurized to 0.3 MPa under a flow of 50 mL/min $N_2$. After stabilization the reduction step is started by flowing a stream of $H_2$ at a rate of 50 mL/min for 3 h. Thereafter the $H_2$ flow is stopped and replaced by a flow of $N_2$. The reactor temperature is cooled down to 280° C. After stabilization, a 50 mL/min flow of CO is introduced and this carburization step lasts 3 h. Then, the reactor temperature is raised at a rate of 1° C./min to the FTO reaction temperature of 340° C. and the pressure is raised to 2 MPa at a rate of 0.015 MPa/min. The conditioning/reaction mixture comprising a CO flow of 25 mL/min, $H_2$ flow of 25 mL/min and He flow of 5 mL/min is introduced at a rate of 1 mL/min. Reaction is maintained for 10 days. After 46 h, the CO conversion reaches 79.7%.
(1) Reduction in $H_2$ at 340° C., 0.3 MPa
(2) Carburization in CO at 280° C., 0.3 MPa
(3) Conditioning at 340° C., 2 MPa Example 3

The CAT1 (0.414 g) is loaded and diluted as in Example 1. The reactor is heated to 425° C. and pressurized to 0.3 MPa under a flow of 50 mL/min $N_2$. After stabilization the reduction step is started by flowing a stream of $H_2$ at 50 mL/min for 3 h. Then, the $H_2$ flow is stopped and replaced by a flow of $N_2$. The reactor temperature is cooled down to 280° C. After stabilization, a 50 mL/min flow of CO is introduced and this carburization step lasts 3 h. Then, the gas flow is replaced by $N_2$ and pressure is raised to 2 MPa and the temperature to 340° C. under $N_2$. After stabilization a combined flow of CO at 25 mL/min, $H_2$ at 25 mL/min, and He at 5 mL/min is introduced at a rate of 1 mL/min. The break-in period is 67 h and the CO conversion reaches 69%.
(1) Reduction in $H_2$ at 425° C., 0.3 MPa
(2) Carburization in CO at 280° C., 0.3 MPa
(3) Conditioning at 340° C., 2 MPa Example 4

The CAT1 is loaded and diluted as in Example 1, with the remainder of processing being the same except that the $H_2$:CO ratio of the synthesis gas for conditioning is 0.5. The reaction is also conducted at a synthesis gas ratio of 0.5. The break-in period is 50 h and the CO conversion reaches a maximum of 55%.
(1) Reduction in $H_2$ at 425° C., 0.3 MPa
(2) Carburization in CO at 280° C., 0.3 MPa
(3) Conditioning at 280° C., 0.3 MPa ($H_2$:CO=0.5)

Example 5

The catalytic test is performed as in Example 1, except that the $H_2$:CO ratio of the synthesis gas used for conditioning is 3. The reaction is also conducted at a synthesis gas ratio of 3. The break-in period is 25 h and the CO conversion reaches a maximum of 82%.
(1) Reduction in $H_2$ at 425° C., 0.3 MPa
(2) Carburization in CO at 280° C., 0.3 MPa
(3) Conditioning at 280° C., 0.3 MPa ($H_2$:CO=3)

Example 6

The catalytic test is performed as in Example 1, except that the carburization temperature is 200° C. After carburization the CO flow is stopped and replaced by $N_2$ flow. The oven temperature is raised at a rate of 1° C./min to 280° C. Then, synthesis gas is introduced such that the conditioning step is performed at 280° C. The oven temperature is then slowly raised to 340° C. and the pressure is raised at a rate of 0.015 MPa/min to 2 MPa in order to carry out the FTO reaction. Break-in period is 42 h and CO conversion reaches a maximum of 79%.
(1) Reduction in $H_2$ at 425° C., 0.3 MPa
(2) Carburization in CO at 200° C., 0.3 MPa
(3) Conditioning at 280° C., 0.3 MPa Example 7

The catalytic test is performed as in Example 1, except that the carburization temperature is 310° C. After carburization the CO flow is stopped and replaced by $N_2$ flow. The oven temperature is adjusted to 280° C. at a rate of 1° C./min. Then, synthesis gas is introduced so that the conditioning step is performed at 280° C. and 0.3 MPa. The oven temperature is then slowly raised to 340° C., and the pressure is raised at a rate of 0.015 MPa/min to 2 MPa to perform the FTO reaction. The break-in period is 56 h and CO conversion reaches a maximum of 71%.
(1) Reduction in $H_2$ at 425° C., 0.3 MPa
(2) Carburization in CO at 310° C., 0.3 MPa
(3) Conditioning at 280° C., 0.3 MPa

Comparative Example 1

The catalytic test is performed as follows. A fixed amount of CAT1 (0.414 g) is loaded in a tubular reactor and diluted with silicon carbide. The reactor temperature is raised to the FTO reaction temperature of 340° C. and pressure of 2 MPa under $N_2$ flow. Then, the reaction mixture consisting of CO at 25 mL/min, $H_2$ at 25 mL/min, and He at 5 mL/min is introduced at a rate of 1 mL/min. The break-in period is 48 h, but the maximum CO conversion reaches only 14% and rapidly drops below 10%, thereby demonstrating a very low productivity catalyst.
(1) No reduction
(2) No carburization
(3) Conditioning at 340° C., 2 MPa

Comparative Example 2

Loading and dilution of the CAT1 is done as in Example 1. The reactor is heated to 425° C. and pressurized to 0.3 MPa under a flow of 50 mL/min $N_2$. After stabilization the reduction step is started by flowing a $H_2$ stream at 50 mL/min for 3 h. Then the $H_2$ flow is stopped and replaced by a flow of $N_2$. The reactor temperature is cooled down to 340° C. Then the pressure is raised to 2 MPa and a combined flow of CO at 25 mL/min, $H_2$ at 25 mL/min, and He at 5 mL/min is introduced at a rate of 1 mL/min. The reaction is maintained for more than 200 h. After a break-in period of 92 h, the CO conversion reaches 54%.
(1) Reduction in $H_2$ at 425° C., 0.3 MPa
(2) No carburization
(3) Conditioning at 340° C., 2 MPa

Comparative Example 3

Loading and dilution of the CAT1 is done according to Example 1. The reactor is heated to 425° C. and pressurized to 0.3 MPa under a flow of 50 mL/min $N_2$. After stabilization the reduction step is started by flowing $H_2$ at 50 mL/min for 6 h. Then the $H_2$ flow is stopped and replaced by a flow of $N_2$. The reactor temperature is cooled down to 340° C. Then the pressure is raised to 2 MPa, and a combined flow of CO at 25 mL/min, $H_2$ at 25 mL/min, and He at 5 mL/min is introduced at a rate of 1 mL/min. The reaction is maintained for more than 200 h. CO conversion reaches 56% after a break-in period of 120 h.
(1) Reduction in $H_2$ at 425° C., 0.3 MPa (6 h)
(2) No Carburization
(3) Conditioning at 340° C., 2 MPa

Comparative Example 4

Loading and dilution of the CAT1 is done according to Example 1. The reactor is heated to 340° C. and pressurized to 0.3 MPa under a flow of 50 mL/min $N_2$. After stabilization the reduction step is started by flowing $H_2$ at 50 mL/min for 3 h. After that, the $H_2$ flow is stopped and replaced by a flow of $N_2$. Then the pressure is raised to 2 MPa. Thereafter a combined flow of CO at 25 mL/min, $H_2$ at 25 mL/min, and He at 5 mL/min is introduced at a rate of 1 mL/min. The reaction is maintained for more than 200 h. The CO conversion reaches 31% after a break-in period of 76 h.
(1) Reduction in $H_2$ at 340° C., 0.3 MPa
(2) No carburization
(3) Conditioning at 340° C., 2 MPa

Comparative Example 5

Loading and dilution of the CAT1 is done as in Example 1. The reactor is heated to 280° C. and pressurized to 0.3 MPa under a flow of 50 mL/min $N_2$. After stabilization the carburization step is started by flowing a stream of CO at 50 mL/min for 3 h. Then, the reactor temperature is raised at a rate of 1° C./min to the FTO temperature of 340° C. and the pressure is raised to 2 MPa at a rate of 0.015 MPa/min. During this ramping, a mixture of CO at 25 mL/min, $H_2$ at 25 mL/min, and He at 5 mL/min is introduced at a rate of 1 mL/min. Break-in time is 75 h, and CO conversion reaches 51%.
(1) No reduction
(2) Carburization in CO at 280° C., 0.3 MPa
(3) Conditioning at 280° C., 0.3 MPa

Comparative Example 6

Loading and dilution of the CAT1 is done as in Example 1. The reactor is heated to 340° C. and pressurized to 0.3 MPa under a flow of $N_2$ at 50 mL/min. After stabilization the reduction step is started by flowing a stream of $H_2$ at 50 mL/min for 3 h. Then, the $H_2$ flow is stopped and replaced by a flow of $N_2$. The reactor temperature is kept at 340° C. and a flow of CO at 50 mL/min is introduced. This carburization step lasts 3 h. Then, the pressure is raised to 2 MPa at a rate of 0.015 MPa/min. During this ramping, a reaction mixture of CO at 25 mL/min, $H_2$ at 25 mL/min, and He at 5 mL/min is introduced at a rate of 1 mL/min. The reaction is maintained for 10 days. There is no break-in period, and after 17 h the CO conversion reaches 46% but then drops rapidly to 37%.
(1) Reduction in $H_2$ at 340° C., 0.3 MPa
(2) Carburization in CO at 340° C., 0.3 MPa
(3) Conditioning at 340° C., 0.3 MPa

Comparative Example 7

Loading and dilution of the CAT1 is done as in Example 1. The reactor is heated to 425° C. and pressurized to 0.3 MPa under a flow of $N_2$ at 50 mL/min. After stabilization the reduction step is started by flowing a stream $H_2$ at 50 mL/min for 3 h. After that, the $H_2$ flow is stopped and replaced by a flow of $N_2$. The reactor temperature is kept at 340° C. and a 50 mL/min flow of CO is introduced. This carburization step lasts 3 h. Then, the pressure is raised to 2 MPa at a rate of 0.015 MPa/min. During this ramping, the following reaction mixture is introduced at a rate of 1 mL/min: CO flow of 25 mL/min, $H_2$ flow of 25 mL/min and He flow of 5 mL/min. The reaction is maintained for over 200 h. After a break-in period of 110 h, the CO conversion reaches 35%.
(1) Reduction in $H_2$ at 425° C., 0.3 MPa
(2) Carburization in CO at 340° C., 0.3 MPa
(3) Conditioning at 340° C., 2 MPa

Comparative Example 8

Loading and dilution of CAT1 is done according to Example 1. The reactor is heated to 425° C. and pressurized to 0.3 MPa under a 50 mL/min flow of $N_2$. After stabilization the reduction step is started by flowing a stream of $H_2$ at 50 mL/min for 3 h. After that, the $H_2$ flow is stopped and replaced by a flow of $N_2$. The reactor temperature is kept at 280° C. and pressure at 0.3 MPa. A reaction mixture is introduced at a rate of 1 mL/min: CO flow of 25 mL/min, $H_2$ flow of 25 mL/min, and He flow of 5 mL/min. This carburization step in synthesis gas lasts 3 h. Then, the pressure is raised to 2 MPa at a rate of 0.015 MPa/min. There is no break-in period, but the CO conversion reaches only 33% and rapidly drops thereafter. The spent catalyst is recovered for particle size analysis.
(1) Reduction in $H_2$ at 425° C., 0.3 MPa
(2) Carburization in synthesis gas at 280° C., 0.3 MPa
(3) Conditioning at 280° C., 2 MPa Comparative Example 9

The catalytic test is performed as in Example 4, except that no carburization step is applied. Once reduced the catalyst is flushed under nitrogen and the operating conditions are adjusted such that the conditioning step is applied at 340° C. and 2 MPa, using a synthesis gas having an $H_2$:CO ratio of 0.5. The break-in period is 63 h and the CO conversion reaches a maximum of 31%.
(1) Reduction in $H_2$ at 425° C., 0.3 MPa
(2) No carburization
(3) Conditioning at 340° C., 2 MPa ($H_2$:CO=0.5)

Comparative Example 10

The catalytic test is performed as in Example 5, except that no carburization step is applied. Once reduced the catalyst is flushed under $N_2$ and the operating conditions are adjusted such that the conditioning step is applied at a $H_2$:CO syngas ratio of 3, at 340° C. and 2 MPa. The break-in period is 30 h and the CO conversion reaches a maximum of 77%. Past the maximum conversion point the catalyst deactivation rate is 0.84%/h.
(1) Reduction in $H_2$ at 425° C., 0.3 MPa
(2) No carburization
(3) Conditioning at 340° C., 2 MPa ($H_2$:CO=3)

Example 8

Loading and dilution of CAT1 is done as in Example 1. The reactor is heated to 300° C. and pressurized to 0.3 MPa under a flow of 50 mL/min nitrogen ($N_2$). After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. for stabilization purposes. Following stabilization, a 50 mL/min flow of CO is introduced for carburization and this carburization step is continued for 3 h. Then, the reactor temperature is raised at a rate of 8° C./min to the predetermined FTO reaction temperature of 340° C. and the pressure is raised to 2 MPa at a rate of 0.015 MPa/min. The following conditioning/reaction mixture (i.e., the synthesis gas) is introduced with CO flow of 25 mL/min, $H_2$ flow of 25 mL/min and He flow of 5 mL/min, i.e., the $H_2$:CO ratio is 1. The reaction is maintained for 7 days. The break-in period is less than 10 h and CO conversion starts at a maximum of 51% and with time decreases.
(1) Reduction in $H_2$ at 300° C., 0.3 MPa
(2) Carburization in CO at 280° C., 0.3 MPa
(3) Conditioning at 280° C., 0.3 MPa Example 9

Loading and dilution of CAT1 is done according to Example 1. The reactor is heated to 475° C. and pressurized to 0.3 MPa under a flow of 50 mL/min $N_2$. After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. for stabilization purposes. Following stabilization, a 50 mL/min flow of CO is introduced for carburization and this carburization step is continued for 3 h. Then, the reactor temperature is raised at a rate of 8° C./min to the predetermined FTO reaction temperature of 340° C. and the pressure is raised to 2 MPa at a rate of 0.015 MPa/min. The following conditioning/reaction mixture (i.e., the synthesis gas) is introduced with a CO flow of 25 mL/min, $H_2$ flow of 25 mL/min and He flow of 5 mL/min, i.e., the $H_2$:CO ratio is 1. The reaction is maintained for 7 days. The break-in period is 110 h and maximum CO conversion is 51%.
(1) Reduction in $H_2$ at 475° C., 0.3 MPa
(2) Carburization in CO at 280° C., 0.3 MPa
(3) Conditioning at 280° C., 0.3 MPa Comparative Example 11

Loading and dilution of the CAT1 is according to Example 1. The reactor is heated to 300° C. and pressurized to 0.3 MPa under a flow of 50 mL/min $N_2$. A reduction step is started by flowing $H_2$ at 50 mL/min for 3 h. After that, the $H_2$ flow is stopped and replaced by a flow of $N_2$. Then the pressure is raised to 2 MPa and the temperature is raised to 340° C. at a rate of 8° C./min. Then, a combined flow of CO at 25 mL/min, $H_2$ at 25 mL/min, and He at 5 mL/min is introduced. The reaction is maintained for over 170 h. The break in period is less than 24 h, the CO conversion reaches 41% goes through a minimum CO conversion of 35% at 33 h, then through a local conversion maximum of 38% at 65 h, and then with time the conversion decreases to just 27% at 173 h.
(1) Reduction in $H_2$ at 300° C., 0.3 MPa
(2) No carburization
(3) Conditioning at 340° C., 2 MPa Comparative Example 12

Loading and dilution of the CAT1 is according to Example 1. The reactor is heated to 475° C. and pressurized to 0.3 MPa under a flow of 50 mL/min $N_2$. After stabilization the reduction step is started by flowing $H_2$ at 50 mL/min for 3 h. After that, the $H_2$ flow is stopped and replaced by a flow of $N_2$. The reactor is cooled to 340° C. Then the pressure is raised to 2 MPa. Then, a combined flow of CO at 25 mL/min, $H_2$ at 25 mL/min, and He at 5 mL/min is introduced. The reaction is maintained for over 170 h. The break in period is less than 24 h, the CO conversion reaches 14% and then with time the conversion decreases to 0% at 170 h.
(1) Reduction in $H_2$ at 475° C., 0.3 MPa
(2) No carburization
(3) Conditioning at 340° C., 2 MPa TABLE 1 summarizes Examples 1-9 and Comparative Examples 1-12.

FIG. 1 provides a visual illustration of the performance of Examples 1-3 and Comparative Examples 1, 2, 3, and 5-8, which highlights some of the significant improvements obtained by the invention.

TABLE 1

| Example (Ex.) or Comparative Example (CEx.) | Reduction temperature (° C.) | Carburization gas, T (° C.) | Conditioning in synthesis gas | | | Break-in period (h) | Maximum conversion (%) |
|---|---|---|---|---|---|---|---|
| | | | $H_2$:CO ratio | T (° C.) | P (MPa) | | |
| Ex. 1 | 425 | CO, 280 | 1 | 280 | 0.3 | 46 | 74 |
| Ex. 2 | 340 | CO, 280 | 1 | 280 | 0.3 | 46 | 80 |
| Ex. 3 | 425 | CO, 280 | 1 | 340 | 2 | 67 | 69 |
| Ex. 4 | 425 | CO, 280 | 0.5 | 280 | 0.3 | 50 | 55 |
| Ex. 5 | 425 | CO, 280 | 3 | 280 | 0.3 | 25 | 82 |
| Ex. 6 | 425 | CO, 200 | 1 | 280 | 0.3 | 42 | 79 |
| Ex. 7 | 425 | CO, 310 | 1 | 280 | 0.3 | 56 | 71 |
| CEx. 1 | N/A | N/A | 1 | 340 | 2 | 48 | 14 |
| CEx. 2 | 425 | N/A | 1 | 340 | 2 | 92 | 54 |
| CEx. 3 | 425 (6 h) | N/A | 1 | 340 | 2 | 120 | 56 |
| CEX. 4 | 340 | N/A | 1 | 340 | 2 | 76 | 31 |
| CEx. 5 | N/A | CO, 280 | 1 | 280 | 0.3 | >70 | 58 |
| CEx. 6 | 340 | CO, 340 | 1 | 340 | 0.3 | N/A | 46 |
| CEx. 7 | 425 | CO, 340 | 1 | 340 | 0.3 | 110 | 35 |
| CEx. 8 | 425 | $H_2$/CO, 280 | 1 | 280 | 0.3 | N/A | 33 |
| CEx. 9 | 425 | N/A | 0.5 | 340 | 2 | 63 | 31 |
| CEx. 10 | 425 | N/A | 3 | 340 | 2 | 30 | 77 |
| Ex. 8 | 300 | CO, 280 | 1 | 280 | 0.3 | <24 followed by deactivation from start | 51 |
| Ex. 9 | 475 | CO, 280 | 1 | 280 | 0.3 | 110 | 51 |
| CEx. 11 | 300 | N/A | 1 | 340 | 2 | <24 followed by deactivation thereafter | 41 |
| CEx. 12 | 475 | N/A | 1 | 340 | 2 | Deactivation from start | 14 |

Example 10 and Comparative Examples 13-15
[CAT2]

Additional examples and comparative examples are prepared based on CAT2, following the protocols shown in TABLE 2 below. The additional experiments all include FT reaction at 2 MPa using a synthesis gas having an $H_2$:CO ratio of 1. In comparison with Example 1, in this set of examples a catalyst is used synthesized with an alpha-alumina that has a support surface area of 10+/−2 $m^2$/g. CAT2 has a similar overall composition as CAT1, but CAT1 is synthesized with an alpha-alumina with a surface area of 1.0+/−0.2 $m^2$/g. A general feature of CAT2 in comparison with CAT1 is that CAT2 has a relatively short break-in time irrespective of treatment of its catalyst precursor composition, with the result that the catalyst treatment method does not a have a distinguishable influence on break-in time. However, a clear effect is observed in the observed maximum conversion and the stability of the catalyst as a function of treatment method.

Based on a comparison of Examples 10 and 11 and Comparative Examples 13 and 14, all obtained at a GHSV of 12,000 $h^{-1}$, the surprisingly beneficial effect of the inventive treatment is evident. Example 8 has the highest conversion at the start and has the least deactivation over time as can be derived from averaged deactivation rate over the first 90 h of reaction. In contrast, Comparative Example 15 is obtained at a lower GHSV of 6,000 $h^{-1}$, which shows a similar conversion as for Example 8. However, the productivity (moles of CO converted per gram of catalyst per hour) for Comparative Example 15 is reduced in comparison with that of Example 8 by a factor of 2. The result of doubling the GHSV of Comparative Example 15 is implied by Comparative Example 14.

Example 10

A fixed amount of CAT2 (0.414 g) is loaded in a tubular reactor and diluted with silicon carbide. The reactor is heated to 425° C. and pressurized to 0.3 MPa under a flow of 50 mL/min nitrogen ($N_2$). After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. for stabilization purposes. The oven temperature is adjusted to 280° C. at a rate of 1° C./min. Then, synthesis gas is introduced such that the conditioning step is performed at 280° C. and 0.3 MPa. The oven temperature is then raised to 340° C. at a rate of 8° C./min, and the pressure is raised at a rate of 0.015 MPa/min to 2 MPa to perform the FTO reaction. CO flow of 50 mL/min, $H_2$ flow of 50 mL/min and He flow of 10 mL/min, i.e., the $H_2$:CO ratio is 1 and GHSV is 12,000 $h^{-1}$. The reaction is maintained for 90 h. The CO conversion reaches a maximum of 94% within the first 5 h and then decreases with an average rate of 0.12%/h over the first 90 h.

(1) Reduction in $H_2$ at 425° C., 0.3 MPa
(2) Carburization in CO at 280° C., 0.3 MPa
(3) Conditioning at 280° C., 0.3 MPa Example 11

The catalytic test is performed as in Example 10, except that the reduction step is performed for 1.3 h instead of 3 h. After reduction the $H_2$ flow is stopped and replaced by $N_2$ flow. The oven temperature is adjusted to 280° C. at a rate of 1° C./min. Then, synthesis gas is introduced such that the conditioning step is performed at 280° C. and 0.3 MPa. The oven temperature is then raised to 340° C. at a rate of 8° C./min, and the pressure is raised at a rate of 0.015 MPa/min to 2 MPa to perform the FTO reaction. The conditioning step is accomplished with a combined flow including CO flow of 50 mL/min, $H_2$ flow of 50 mL/min and He flow of 10 mL/min, i.e., the $H_2$:CO ratio is 1 and GHSV is 12,000 $h^{-1}$. The reaction is maintained for 170 h. The CO conversion reaches a maximum of 92% within the first 5 h and then decreases with an average rate of 0.15%/h over the first 90 h.
(1) Reduction in $H_2$ at 425° C., 0.3 MPa
(2) Carburization in CO at 280° C., 0.3 MPa
(3) Conditioning at 280° C., 0.3 MPa Example 12

The catalytic test is performed as in Example 10, except that the introduction of synthesis gas is done with higher flows. After reduction the $H_2$ flow is stopped and replaced by $N_2$ flow. The oven temperature is adjusted to 280° C. at a rate of 1° C./min. Then, synthesis gas is introduced such that the conditioning step is performed at 280° C. and 0.3 MPa. The oven temperature is raised to 340° C. at a rate of 8° C./min, and the pressure is raised at a rate of 0.015 MPa/min to 2 MPa to perform the FTO reaction. CO flow of 100 mL/min, $H_2$ flow of 100 mL/min and He flow of 10 mL/min, i.e., the $H_2$:CO ratio is 1 and the GHSV is 24,000 $h^{-1}$. The reaction is maintained for 170 h. The CO conversion reaches a maximum of 81% within the first 5 h and then decreases with an average rate of 0.305%/h over the first 90 h.
(1) Reduction in $H_2$ at 425° C., 0.3 MPa
(2) Carburization in CO at 280° C., 0.3 MPa
(3) Conditioning at 280° C., 0.3 MPa Comparative Example 13

Loading and dilution of the CAT2 is done as in Example 10. The reactor is heated to 280° C. and pressurized to 0.3 MPa under a flow of 50 mL/min $N_2$. After stabilization the carburization step is started by flowing a stream of CO at 50 mL/min for 3 h. Then, the reactor temperature is raised at a rate of 8° C./min to the FTO reaction temperature of 340° C. and the pressure is raised to 2 MPa at a rate of 0.015 MPa/min. During this ramping, a mixture of CO at 50 mL/min, $H_2$ at 50 mL/min, and He at 10 mL/min is introduced, i.e., a GHSV of 12,000 $h^{-1}$. The reaction is maintained for 180 h. The CO conversion reaches a maximum of 74% within the first 5 h and then decreases with an average rate of 0.52%/h over the first 90 h.
(1) No reduction
(2) Carburization in CO at 280° C., 0.3 MPa
(3) Conditioning at 280° C., 0.3 MPa Comparative Example 14

Loading and dilution of CAT2 is done as in Example 10. The reactor is heated to 425° C. and pressurized to 0.3 MPa under a flow of 50 mL/min $N_2$. After stabilization the reduction step is started by flowing a $H_2$ stream at 50 mL/min for 3 h. Then the $H_2$ flow is stopped and replaced by a flow of $N_2$. The reactor temperature is cooled to 340° C. Then, the pressure is raised to 2 MPa. Then a combined flow of CO at 50 mL/min, $H_2$ at 50 mL/min, and He at 10 mL/min is introduced. The reaction is maintained for more than 170 h. CO conversion reaches a maximum of 84% within the first 5 h and then decreases with an average rate of 0.26%/h over the first 90 h.
(1) Reduction in $H_2$ at 425° C., 0.3 MPa
(2) No carburization
(3) Conditioning at 340° C., 2 MPa Comparative Example 15

Loading and dilution of CAT2 is done as in Example 10. The reactor is heated to 425° C. and pressurized to 0.3 MPa under a flow of 50 mL/min $N_2$. After stabilization the reduction step is started by flowing a $H_2$ stream at 50 mL/min for 3 h. Then the $H_2$ flow is stopped and replaced by a flow of $N_2$. The reactor temperature is cooled to 340° C. Then, the pressure is raised to 2 MPa. Then a combined flow of CO at 25 mL/min, $H_2$ at 25 mL/min, and He at 5 mL/min is introduced. The reaction is maintained for more than 170 h. CO conversion reaches a maximum of 92% within the first 5 h and then decreases with an average rate of 0.12%/h over the first 90 h.
(1) Reduction in $H_2$ at 425° C., 0.3 MPa
(2) No carburization
(3) Conditioning at 340° C., 2 MPa

TABLE 2

| Example (Ex.) or Comparative Example (CEx.) | Reduction | | | | Carburization | | | Conditioning | | | | Reaction | |
|---|---|---|---|---|---|---|---|---|---|---|---|---|---|
| | T (° C.) | P (MPa) | t (h) | Gas | T (° C.) | P (MPa) | t (h) | T (° C.) | P (MPa) | $H_2$:CO | GHSV ($h^{-1}$) | Max. conversion at t <12 h | Deactivation rate, in first 90 h (%/h) |
| Ex. 10 | 425 | 0.3 | 3 | CO | 280 | 3 | 3 | 280 | 3 | 1 | 12,000 | 94 | 0.12 |
| Ex. 11 | 425 | 0.3 | 1.3 | CO | 280 | 3 | 3 | 280 | 3 | 1 | 12,000 | 92 | 0.15 |
| Ex. 12 | 425 | 0.3 | 3 | CO | 280 | 3 | 3 | 280 | 3 | 1 | 24,000 | 81 | 0.305 |
| CEx. 13 | N/A | N/A | N/A | CO | 280 | 3 | 3 | 280 | 3 | 1 | 12,000 | 74 | 0.52 |
| CEx. 14 | 425 | 0.3 | 3 | N/A | N/A | N/A | N/A | 340 | 20 | 1 | 12,000 | 84 | 0.26 |
| CEx. 15 | 425 | 0.3 | 3 | N/A | N/A | N/A | N/A | 340 | 20 | 1 | 6,000 | 92 | 0.12 |

Examples 13-15 and Comparative Examples 16-18 [CAT3]

Additional catalysts are prepared based on CAT3 and using the treatment protocols specified in TABLE 3. In this case 0.45 mL of CAT3, corresponding to 0.35 g, is employed. FT conditions include pressure at 2 MPa and an $H_2$:CO ratio is at 1. All catalysts are still slowly activating at t=24 h except for Comparative Example 17. For CAT3, applying a higher reduction temperature of 475° C. for 3 h has a beneficial effect, as shown in Example 13 and Example 14. A beneficial effect of the inventive treatment is also observed in comparing Example 14 and Comparative Examples 16 and 17. The CAT3 in Example 11 shows higher maximum conversion than in either Comparative Example 16 or Comparative Example 17. In Example 12 the temperature is higher in the reduction step, and for CAT3 this improves the performance over that shown in Example 8. The beneficial effect of the invention may also be seen, at a lower GHSV, by comparing Example 15 with Comparative Example 18. In Example 15 the break-in time is shorter than for Comparative Example 18. TABLE 3 summarizes this data.

Example 13

A fixed amount of CAT3 (0.35 g) is loaded in a tubular reactor and diluted with silicon carbide. The reactor is heated to 425° C. and pressurized to 0.3 MPa under a flow of 50 mL/min $N_2$. After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. and oven temperature is adjusted to 280° C. at a rate of 1° C./min. Then, synthesis gas is introduced such that the conditioning step is performed at 280° C. and 0.3 MPa. The oven temperature is then raised to 340° C. at a rate of 8° C./min, and the pressure is raised at a rate of 0.015 MPa/min to 2 MPa to perform the FTO reaction with CO flow of 50 mL/min, $H_2$ flow of 50 mL/min and He flow of 10 mL/min, i.e., the $H_2$:CO ratio is 1 and the GHSV is 12,000 $h^{-1}$. The reaction is maintained for 170 h. CO conversion reaches 38% within the first 24 h and then further increases to 53% at 121 h.
(1) Reduction in $H_2$ at 425° C., 0.3 MPa
(2) Carburization in CO at 280° C., 0.3 MPa
(3) Conditioning at 280° C., 0.3 MPa Example 14

Loading and dilution of CAT3 is done as in Example 13. The reactor is heated to 475° C. and pressurized to 0.3 MPa under a flow of 50 mL/min $N_2$. After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. for stabilization purposes. The oven temperature is adjusted to 280° C. at a rate of 1° C./min. Then, synthesis gas is introduced such that the conditioning step is performed at 280° C. and 0.3 MPa. The oven temperature is then raised to 340° C. at a rate of 8° C./min, and the pressure is raised at a rate of 0.015 MPa/min to 2 MPa to perform the FTO reaction with CO flow of 50 mL/min, $H_2$ flow of 50 mL/min and He flow of 10 mL/min, i.e., the $H_2$:CO ratio is 1 and the GHSV is 12,000 $h^{-1}$. The reaction is maintained for 170 h. CO conversion reaches 45% within the first 24 h and then further increases to 58% at 71 h.
(1) Reduction in $H_2$ at 475° C., 0.3 MPa
(2) Carburization in CO at 280° C., 0.3 MPa
(3) Conditioning at 280° C., 0.3 MPa Example 15

Figure 2:
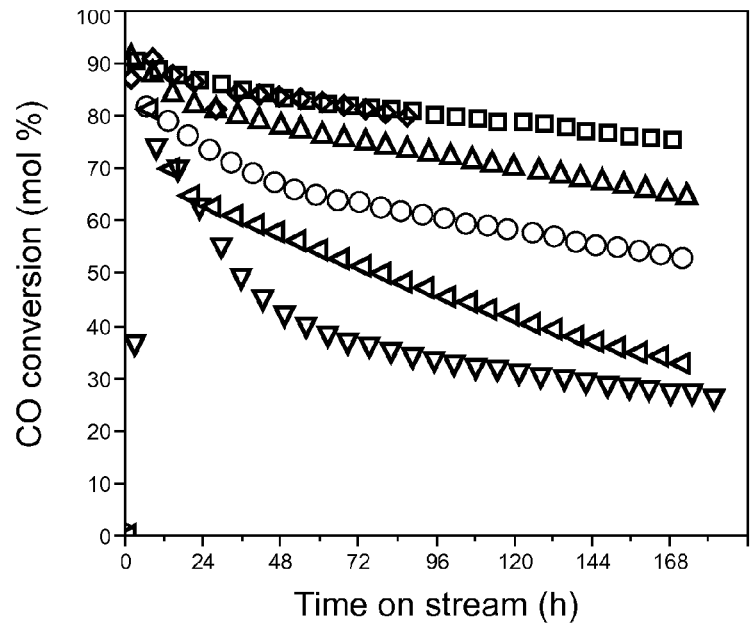
FIG. 2 is a graphic overlay of CO conversion curves as a function of run time during FT conditions (in hours) for a CAT2 treated under different activation conditions.

Loading and dilution of CAT3 is done according to Example 13. The reactor is heated to 425° C. and pressurized to 0.3 MPa under a flow of 50 mL/min $N_2$. After stabilization a $H_2$ stream is flowed at 50 mL/min for 3 h for the reduction step. Thereafter, the $H_2$ flow is stopped and replaced by a flow of $N_2$. The reactor temperature is cooled down to 280° C. for stabilization purposes. The oven temperature is adjusted to 280° C. at a rate of 1° C./min. Then, synthesis gas is introduced such that the conditioning step is performed at 280° C. and 0.3 MPa. The oven temperature is then raised to 340° C. at a rate of 8° C./min, and the pressure is raised at a rate of 0.015 MPa/min to 2 MPa to perform the FTO reaction with CO flow of 25 mL/min, $H_2$ flow of 25 mL/min and He flow of 5 mL/min, i.e., the $H_2$:CO ratio is 1 and GHSV is 6,000 $h^{-1}$. The reaction is maintained for 170 h. CO conversion reaches 57% within the first 24 h and then further increases to a maximum level of 75% at 126 h.
(1) Reduction in $H_2$ at 425° C., 0.3 MPa
(2) Carburization in CO at 280° C., 0.3 MPa
(3) Conditioning at 280° C., 0.3 MPa FIG. 2 provides a visual illustration of the performance of Examples 10-12 and Comparative Examples 13-15, which highlights some of the significant improvements obtained by the invention.

Comparative Example 16

Loading and dilution of CAT3 is done as in Example 13. The reactor is heated to 425° C. and pressurized to 0.3 MPa under a flow of 50 mL/min $N_2$. After stabilization the reduction step is started by flowing a $H_2$ stream at 50 mL/min for 3 h. Then $H_2$ flow is stopped and replaced by a flow of $N_2$. The reactor temperature is cooled to 340° C. Then, the pressure is raised to 2 MPa. Then a combined flow of CO at 50 mL/min, $H_2$ at 50 mL/min, and He at 10 mL/min is introduced. The reaction is maintained for more than 170 h. CO conversion reaches 29% within the first 24 h and then further increases to a maximum level of 47% at 138 h.
(1) Reduction in $H_2$ at 425° C., 0.3 MPa
(2) No carburization
(3) Conditioning at 340° C., 2 MPa Comparative Example 17

Loading and dilution of the CAT3 is done as in Example 13. The reactor is heated to 280° C. and pressurized to 0.3 MPa under a flow of 50 mL/min $N_2$. After stabilization the carburization step is started by flowing a stream of CO at 50 mL/min for 3 h. Then, the reactor temperature is raised at a rate of 8° C./min to the FTO reaction temperature of 340° C. and the pressure is raised to 2 MPa at a rate of 0.015 MPa/min. During this ramping, a mixture of CO at 50 mL/min, $H_2$ at 50 mL/min, and He at 10 mL/min is introduced. The reaction is maintained for 180 h. CO conversion reaches a maximum of 17% within the first 24 h and then the conversion level continues to decrease to 12% after 168 h.
(1) No reduction
(2) Carburization in CO at 280° C., 0.3 MPa
(3) Conditioning at 280° C., 0.3 MPa Comparative Example 18

Figure 3:
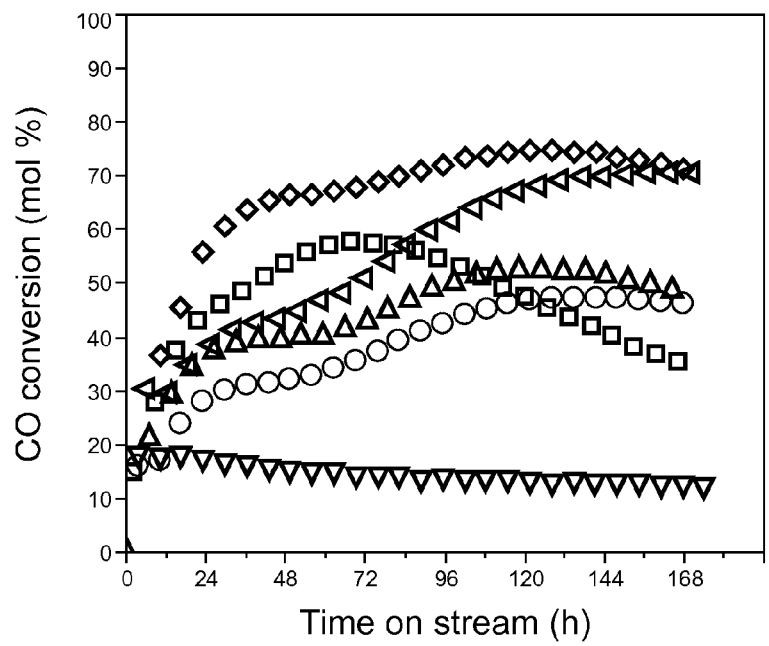
FIG. 3 is a graphic overlay of CO conversion curves as a function of run time (in hours) for a CAT2 treated under different activation conditions.

Loading and dilution of CAT3 is done as in Example 13. The reactor is heated to 425° C. and pressurized to 0.3 MPa under a flow of 50 mL/min $N_2$. After stabilization the reduction step is started by flowing a $H_2$ stream at 50 mL/min for 3 h. Then the $H_2$ flow is stopped and replaced by a flow of $N_2$. The reactor temperature is cooled to 340° C. Then, the pressure is raised to 2 MPa. Then a combined flow of CO at 25 mL/min, $H_2$ at 25 mL/min, and He at 5 mL/min is introduced. The reaction is maintained for more than 170 h. CO conversion starts at 50%, then drops and reaches 38% at 24 h, and then increases to a maximum level of 71% at 168 h.
(1) Reduction in $H_2$ at 425° C., 0.3 MPa
(2) No carburization
(3) Conditioning at 340° C., 2 MPa FIG. 3 provides a visual illustration of the performance of Examples 13-15 and Comparative Examples 16-18, which highlights some of the significant improvements obtained by the invention.

TABLE 3

| | Reduction | | | | Carburization | | | Syngas introduction | | | | Reaction | | | |
|---|---|---|---|---|---|---|---|---|---|---|---|---|---|---|---|
| | | | | | | | | | | | | | | Time at | |
| | | | | | | | | | | | | | Max. | max. | Conversion |
| Ex or CEx. | T (° C.) | P MPa | t (h) | Gas | T (° C.) | P MPa | t (h) | T (° C.) | P MPa | $H_2$:CO | GHSV ($h^{-1}$) | Conversion at t = 24 h | conversion (%) | conversion (h) | at t = 168 h |
| Ex. 13 | 425 | 3 | 3 | CO | 280 | 3 | 6 | 280 | 3 | 1 | 13300 | 38 | 53 | 121 | 49 |
| Ex. 14 | 475 | 3 | 3 | CO | 280 | 3 | 6 | 280 | 3 | 1 | 13300 | 45 | 58 | 71 | 36 |
| Ex. 15 | 425 | 3 | 3 | CO | 280 | 3 | 6 | 280 | 3 | 1 | 6700 | 57 | 75 | 126 | 71 |
| CEx. 16 | 425 | 3 | 3 | N/A | N/A | N/A | N/A | 340 | 20 | 1 | 13300 | 29 | 47 | 138 | 46 |
| CEx. 17 | N/A | N/A | N/A | CO | 280 | 3 | 6 | 280 | 3 | 1 | 13300 | 17 | 18 | 13 | 12 |
| CEx. 18 | 425 | 3 | 3 | N/A | N/A | N/A | N/A | 340 | 20 | 1 | 6,700 | 38 | −71 | 168 | 71 |

N/A = not applicable

TEM Analysis

Figure 4:
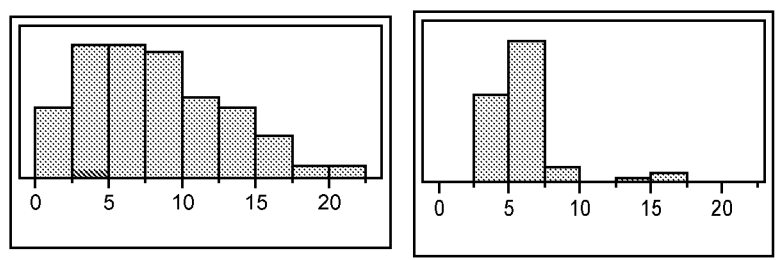
FIG. 4 shows a graphic analysis of TEM micrographs to determine particle size distributions for Example 1 and Comparative Example 8. Graph on left shows Comparative Example 8 and graph on right shows Example 1.

A comparison is carried out via transmission electron microscopy (TEM) to determine the iron-containing particle size distributions for the spent catalyst used in Example 1 and that used in Comparative Example 8. The overall treatments of the two are similar except that in Example 1 the carburization step (step 2) is carried out using a pure CO atmosphere, while in Comparative Example 8, the carburization step is carried out using an $H_2$:CO mixture having a 1:1 volume ratio. More than 100 particles are measured randomly for each catalyst sample. The particle size distribution is shown in FIG. 4. By applying a log-normal fit it is determined that the catalyst from Example 1 has a mean particle size of 5.4 nm+/−0.5 nm, with 90 wt % of the particles falling within a size range from 2 nm to 9 nm, or more specifically, from 2.9 nm to 8.8 nm. The catalyst obtained from Comparative Example 8 has a mean particle size of 7.9 nm+/−0.9 nm with 90 wt % of the particles falling within a size range from 2.1 nm to 19.5 nm.

The invention claimed is:

1. A process for producing a catalyst comprising sequential steps in order as follows:
   (1) subjecting a catalyst precursor composition that comprises iron oxide and at least one alkali metal, and optionally, at least one alkaline earth metal, on a particulate support,
   the iron oxide being present in an amount ranging from 1 percent by weight to 20 percent by weight, based upon the combined weight of iron and the particulate support,
   the alkali metal being present in an amount ranging from greater than 0 mole percent to 10 mole percent, based on moles of iron in the iron-containing compound, and the alkaline earth metal being in an amount ranging from 0 mole percent to 10 mole percent, based upon the combined weight of the iron-containing compound and the support,
   to reduction in a first atmosphere containing hydrogen at a hydrogen pressure ranging from 0.1 megapascal to 1 megapascal, at a temperature from 300° C. to 475° C.
   to form an at least partially reduced catalyst precursor composition;
   (2) subjecting the at least partially reduced catalyst precursor composition to carburization in a second atmosphere having a composition containing at least 50 volume percent carbon monoxide and less than 10 volume percent hydrogen,
   at a carbon monoxide pressure ranging from 0.1 megapascal to 1 megapascal
   at a temperature ranging from 200° C. to less than 340° C., to form an at least partially carburized catalyst precursor composition; and
   (3) subjecting the at least partially carburized catalyst precursor composition to conditioning
   in an atmosphere containing hydrogen and carbon monoxide
   in a molar ratio ranging from 0.5 to 3,
   wherein there is a maximum of 50 volume percent of inert gas, and
   wherein the combined hydrogen and carbon monoxide pressures total ranges from 0.1 megapascal to 2 megapascals,
   at a temperature ranging from 200° C. to 340° C.,
   to form an at least partially conditioned, particulate catalyst that comprises iron carbide.

2. The process of claim 1 wherein the alkali metal is selected from potassium and sodium.

3. The process of claim 1 wherein the particulate support comprises a material selected from an alpha-alumina, titania, zirconia, silicon carbide, carbon nanofibers, and combinations thereof.

4. The process of claim 3 wherein the material is an alpha-alumina, titania, or zirconia having a surface area of less than 100 square meters per gram; a silicon carbide or carbon nanofiber having a surface area of less than 500 square meters per gram; or a combination thereof.

5. A catalyst composition prepared by the process of claim 1.

6. The catalyst according to claim 5, wherein the catalyst has a break-in period that is shorter by at least 20 percent than that of a catalyst prepared from an identical catalyst precursor composition, but without at least one of step (1) and step (2).

7. The catalyst according to claim 5, wherein the catalyst has a maximum carbon monoxide conversion percentage that is greater by at least 10% percent than that of a catalyst prepared from an identical catalyst precursor composition, but without at least one of step (1) and step (2).

8. The catalyst according to claim 5, wherein the catalyst has a deactivation rate that is reduced by at least 50 percent when compared with than that of a catalyst prepared from an identical catalyst precursor composition, but without at least one of step (1) and step (2).

9. The catalyst according to claim 5, wherein the at least partially conditioned, particulate catalyst is characterized as having
   (1) a mean particle size ranging from five nanometers to seven nanometers, and (2) a particle size distribution wherein at least ninety weight percent of the catalyst particles have a particle size ranging from two nanometers to nine nanometers.

10. A Fischer-Tropsch process comprising:

subjecting the catalyst composition according to claim 5 to high temperatures, wherein high temperature is defined by 300° C. to 350° C.

\* \* \* \* \*